United States Patent
Alpert et al.

(10) Patent No.: US 11,911,200 B1
(45) Date of Patent: Feb. 27, 2024

(54) CONTEXTUAL IMAGE CROPPING AND REPORT GENERATION

(71) Applicant: Amazon Technologies, Inc., Seattle, WA (US)

(72) Inventors: Sharon Alpert, Rehovot (IL); Antonio Criminisi, Cambridge (GB)

(73) Assignee: Amazon Technologies, Inc., Seattle, WA (US)

(*) Notice: Subject to any disclaimer, the term of this patent is extended or adjusted under 35 U.S.C. 154(b) by 492 days.

(21) Appl. No.: 17/001,982

(22) Filed: Aug. 25, 2020

(51) Int. Cl.
*G06T 7/00* (2017.01)
*A61B 5/103* (2006.01)
*A61B 8/08* (2006.01)
*G06T 7/11* (2017.01)
*G10L 15/22* (2006.01)
*G16H 10/00* (2018.01)
*G16H 15/00* (2018.01)
*G16H 30/40* (2018.01)
*G16H 50/00* (2018.01)

(52) U.S. Cl.
CPC ............. *A61B 6/468* (2013.01); *G06T 7/11* (2017.01); *G10L 15/22* (2013.01); *G16H 15/00* (2018.01); *G16H 30/40* (2018.01); *G06T 2207/20132* (2013.01); *G10L 2015/223* (2013.01)

(58) Field of Classification Search
USPC ............ 382/128–134, 152–159, 181–229
See application file for complete search history.

(56) References Cited

U.S. PATENT DOCUMENTS

| | | | | |
|---|---|---|---|---|
| 11,553,887 | B2* | 1/2023 | McLaughlin | A61B 6/5205 |
| 2012/0316874 | A1* | 12/2012 | Lipman | G16H 15/00 704/235 |
| 2013/0326386 | A1 | 12/2013 | Vendrell | |
| 2017/0154156 | A1* | 6/2017 | Sevenster | G06F 40/174 |
| 2018/0055468 | A1* | 3/2018 | Reicher | A61B 5/743 |
| 2019/0138805 | A1 | 5/2019 | Saha et al. | |
| 2020/0126648 | A1* | 4/2020 | Schadewaldt | G16H 30/40 |
| 2020/0160982 | A1* | 5/2020 | Gurson | G06N 3/045 |
| 2020/0202523 | A1* | 6/2020 | Ahn | G06F 18/285 |
| 2020/0357117 | A1* | 11/2020 | Lyman | G06T 7/0012 |
| 2021/0074427 | A1* | 3/2021 | Xu | G16H 10/60 |
| 2021/0125706 | A1* | 4/2021 | Spottiswoode | G06V 10/82 |
| 2021/0166805 | A1* | 6/2021 | Knoplioch | G06T 7/0012 |
| 2021/0259664 | A1* | 8/2021 | Hare | G16H 40/63 |
| 2021/0313045 | A1* | 10/2021 | Wu | G06V 10/764 |
| 2021/0366106 | A1* | 11/2021 | Yao | G06N 3/0454 |

OTHER PUBLICATIONS

U.S. Appl. No. 17/217,675, U.S. Patent Application, "Methods and Systems for Detection of Errors in Medical Reports," filed Mar. 30, 2021.

* cited by examiner

Primary Examiner — Marcellus J Augustin
(74) Attorney, Agent, or Firm — Kilpatrick Townsend & Stockton LLP

(57) ABSTRACT

Systems and techniques for producing image-based radiology reports including contextual cropping of image data and radiologist supplied notes and annotations are provided herein. Computer vision and natural language processing algorithms may enable processing of image data and language inputs to identify objects associated with annotations, aid in cropping the image data according to the annotations and object identification and in producing a final text and image laden report.

19 Claims, 9 Drawing Sheets

CONTEXTUAL IMAGE CROPPING AND REPORT GENERATION

BACKGROUND

Medical images are used extensively in disease diagnosis, treatment, monitoring, and drug discovery. Medical reports typically include written plain text descriptions of findings and results of medical tests and imaging. Radiologists read medical images to observe abnormalities and make diagnosis of diseases. Writing diagnosis report is also part of routine jobs for radiologists/operators. For example, medical diagnosis reports describe and summarize important findings in medical images such as x-ray images, Computed Tomography (CT) images, Magnetic Resonance Imaging (MRI) images, ultrasound images and the like.

In recent years, the amount of medical image data obtained in one examination has increased since performance of medical image acquisition apparatuses has improved. Therefore, compiling a radiology report requires much time. Also, reports are typically not quantitative, nor sufficiently expressive.

BRIEF DESCRIPTION OF THE DRAWINGS

Various embodiments in accordance with the present disclosure will be described with reference to the drawings, in which.

DETAILED DESCRIPTION

Figure 1:
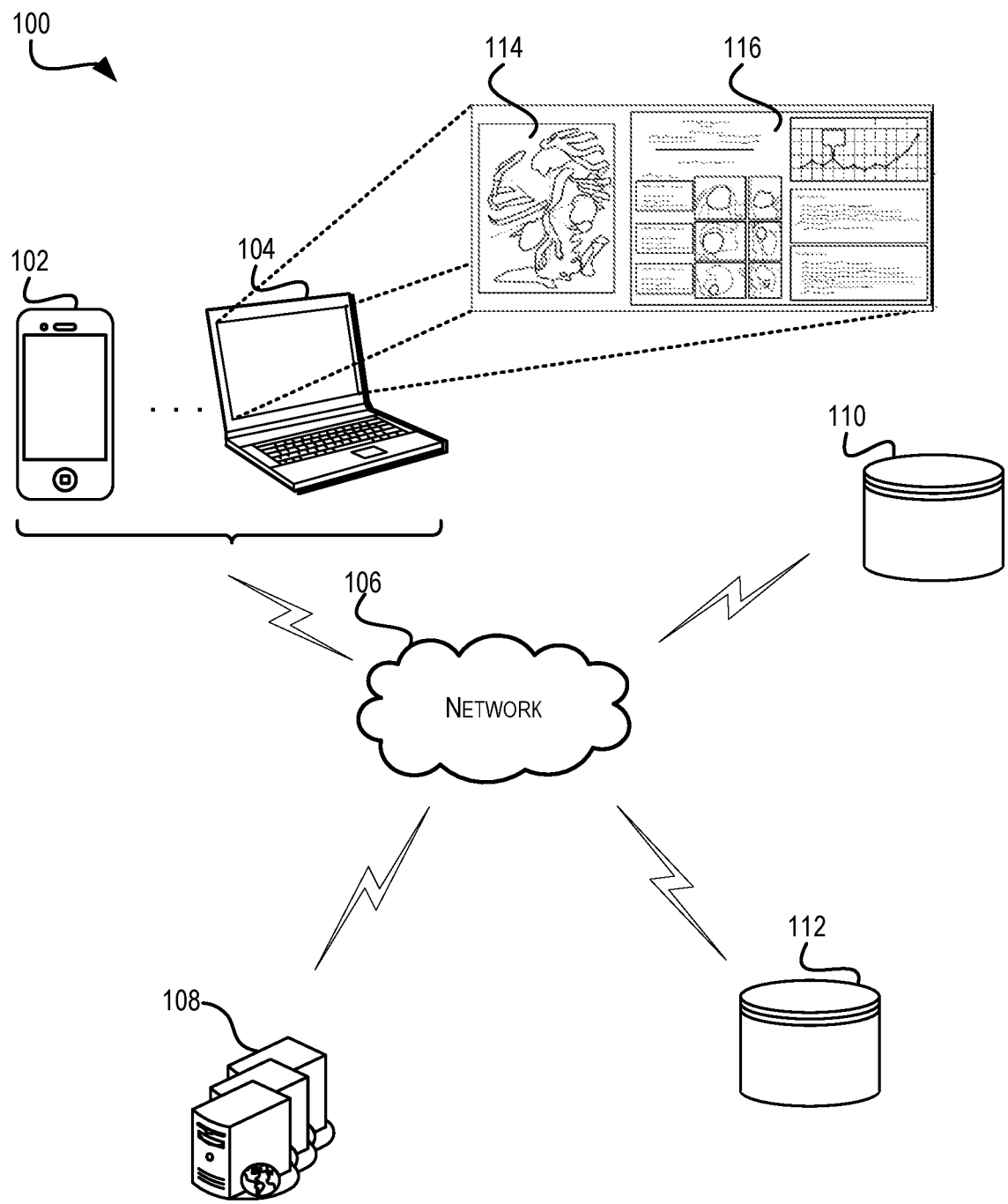
FIG. 1 illustrates an example system diagram for elements of a system for generating a medical report.

Techniques described herein include systems and processes by which a medical report can be generated based upon medical images. The techniques described herein aid medical personnel in analyzing, annotating, and generating easy-to-understand medical reports. The systems and techniques described herein provide for real-time generation of medical reports combining image data from an imaging device and speech input from an input device. Through a graphical user interface ("GUI"), generation of medical reports is enabled that are image-rich and including contextually cropped medical images. The GUI further enables generation of the medical reports based on user speech into a user device. Specifically, the user device enables dictation and creation of medical reports using spoken language including both instructions and report contents. The systems and techniques also enable contextual cropping of medical images and inclusion of the cropped images in the medical report. Contextual cropping of medical images reduces the amount of image data by cropping the image in an area of interest and also maintains information such that a viewer can understand the surrounding context and placement of the cropped image in the overall medical images.

By way of illustration, consider a scenario in which the system is implemented by a user with one or more computing devices. In this scenario, the user may be a medical professional charged with generating a report based on medical images of a patient. The GUI enables the user to add, view, or edit annotations within the medical images, such as markers identifying areas of interest or measurements of anatomy. The system enables cropping of the medical images such that the context surrounding individual annotations is preserved for inclusion in the medical report. The system crops the medical images to preserve the context by using computer vision algorithms to identify objects, such as anatomy or anomalies of interest, within the medical images and crop the medical images such that a user or viewer can observe the cropped image and understand the surrounding context without including the entirety of the medical image. In some cases, the system crops the images based solely on features within the image, as identified by computer vision or other algorithms, such as features defining boundaries of objects. The GUI further enables generation of a medical report including the cropped medical images and user-provided notes and description. The GUI enables the user to generate such a report through use of spoken language as the user dictates report generation instructions as well as contents for inclusion in the medical report.

The description included herein provides several improvements over past and conventional systems, including medical image cropping and report generation systems. In particular, the description herein enables contextual cropping of medical images around medical professional annotations to direct attention to an area of interest while preserving context and surrounding information for clear understanding of the annotation. The system provides an improved user experience for generating medical reports that is intuitive and simple for a user to provide information and automatically generate a report as the user dictates information to the system. For example, the system enables automatic selection and inclusion of cropped medical images in a report based on natural language processing of user-provided information in the report. The system also enables a user to provide report generation instructions, such as to include a particular medical image, with information to fill the body of the report at the same time, in the same manner, and without differentiating what constitutes report generation instructions and what constitutes report content. In addition to efficiency and productivity improvements over conventional systems, reports generated using the systems and techniques herein will save time with operators especially in complicated cases like oncology which require repeated visits by the patient and repeated interpretations of medical images. The operator, for example would have to access a database less frequently as the pertinent information will be directly included in the report. An image-rich report which can measure small changes in tumors serves the dual purpose of saving the operator time as well as potentially increasing the patient experience. With improved information flow, treatment can be optimized for the patient. The GUI of systems described herein provides an improved user experience for generating medical reports as the GUI is intuitive and simple for a user to provide information and report generation instructions through dictation and the GUI enables automatic generation of a report in real-time as the user dictates information to the system, enabling easy editing and proofreading. Additionally, the description herein provides scalable inclusion of future algorithms and features to continually improve and increase the ease and speed of generating image-rich medical reports. For example, a set of algorithms may initially be included with the systems herein though the associated algorithms may be updated to include additional algorithms or more refined algorithms to detect additional information, process image and speech information, and identify additional general and disease-specific features within medical images. In such examples, the algorithms may provide significant data analysis of the medical images and reduce a burden on a radiologist. The radiologist may then focus their time and attention to providing meaningful analysis of results and an improved final medical report.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

FIG. 1 illustrates an example system diagram for elements of a system 100 for generating a medical report. The system 100 includes one or more user devices 102 and 104, a remote computing device 108, a first database 110, and a second database 112. The system 100 includes a network 106 that provides communication between the various elements. The network 106 may be wired or wireless and may include elements such as the internet. Initially, medical images of a patient are stored on the first database 110 awaiting analysis by a radiologist and generation of a report. When the radiologist begins working on a particular case, they access the image data from the first database 110 over the network 106. The image data is viewable on the user device 104 using systems and methods described herein to generate a report. The user device 104 and the user device 102 are in communication with one another such that the user device 102 may be used to control some actions with respect to the generation of the report on the user device 104. For example, the user device 102 may be a smartphone while the user device 104 is a personal computer. The user device 102 may meet FDA and other requirements including privacy requirements and secure patient information as part of the system, while conventional systems were limited to FDA-approved devices, the systems and methods described herein enable use of user devices such as smartphones with an FDA approved computing device used by the user. The user device 102 may include a voice input device and on a graphical user interface ("GUI") thereof, may include options for the user to interact with the report generation software on the user device 104.

Through the user devices 102 and 104, the user is able to generate a report 116 based on and including selections from the medical images 114 in real-time as the user dictates report content as well as report generation instructions into the user device 102. As the user dictates instructions into the user device 102, the report 116 is generated in real-time either based on natural language processing of commands included in the dictation, or by determining, based on the contents of the dictated information from the user, a report format and information such as image information to be included in the report 116.

The user is able to make annotations within the image data 114 or view previously made annotations, and includes computer vision algorithms to aid in gathering information and data from the image data as the user analyzes. The computer vision algorithms also aid in generation of the report and can be used to identify anatomy, annotations, or other features within the image data for selection and inclusion within the report. In some examples, a contextual cropping algorithm may determine a size and placement of a cropping window around a particular annotation or anatomy to crop the image data 114 and include the cropped image in the body of the report 116, providing an image-rich medical report with helpful context around each annotation or anatomy feature preserved for ease of viewing and understanding at subsequent stages.

In some examples, the user devices 102 and 104 may perform the functions of the techniques and methods described herein. In some examples, processing of data or some operations may be performed at the remote computing device 108, such as a cloud computing device or remote server. In some examples, processing may be distributed and shared between the user devices 102 and 104 and the remote computing device 108.

Following generation of the report, the report is exported to the second database 112 for storage and later access in connection with treatment of a patient. The second database 112 may be part of the first database 110. In some examples, the second database 112 may be an existing database used to store text-only medical reports in a particular format. The systems and methods described herein provide for exporting of the medical report 116 in a format compatible with storage in such databases, without the need to revamp the storage requirements or alter file types and report reading software across a care network, such as a hospital.

In a conventional process of providing a medical report, medical images of a patient are initially gathered using an imaging device. The imaging device may include any suitable device for capturing image data associated with a patient. In some examples the imaging device may include x-ray machines, computed tomography machines, magnetic resonance imaging machines, or other such imaging devices. The image data from the imaging device is stored in a database for access by a second operator. The second operator reviews the image data accessed from the database and dictates or types a report using a reporting tool. The report includes findings and notes of the second operator based on the image data. The report is text-only and does not include any of the image data. The report is subsequently stored in a database, which may be the same database or a separate database from database. An operator then accesses the report from the database to decide on treatment for the patient. The process is a manual process that requires inefficient manual generation of a text-only report. An operator typically expends further time and effort to view the image data separately from the report. Reports that include image data and further information than available in text-only reports increase the speed, efficiency, and quality of care provided by the operator.

Figure 2:
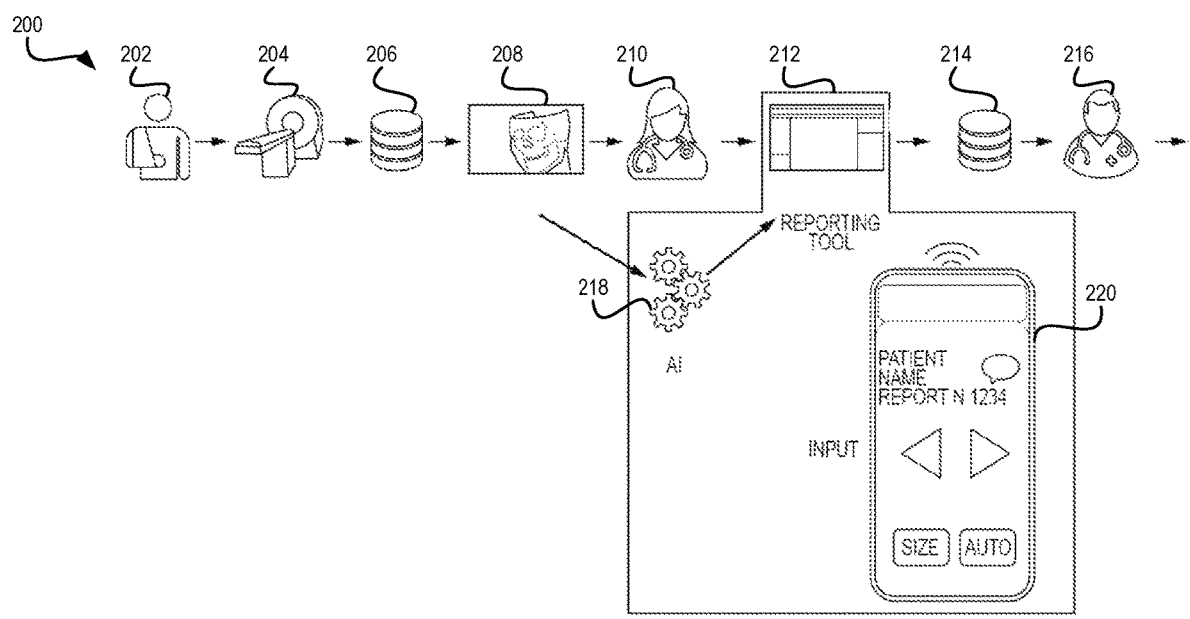
FIG. 2 illustrates an example flow for generating a medical report using a report generation system, according to at least some examples.

FIG. 2 illustrates an example flow for a process 200 for generating a medical report using a report generation system, according to at least some examples. The process 200 provides a streamlined and efficient manner to produce reports through an intuitive tool as well as providing additional details to an operator 216 not typically included in previous reports that aids the operator 216 in making treatment decisions for a patient 202. The intuitive tool may include a GUI that is easy to navigate and operate and provides significant advantages over conventional processes that result in faster processing of medical reports and more informative and useful medical reports.

The process 200 begins similar to a conventional process, with image data 208 of a patient 202 gathered using an imaging device 204 and storing the image data on a database 206. The second operator 210 is enabled to more efficiently and quickly produce image-rich and beneficial reports in a similar workflow without significant disruption or additional training. In particular, an artificial intelligence ("AI") system 218 is implemented on a computing resource in communication with the reporting tool 212 and a user device 220, provides a better reporting tool that includes automatic image analysis using computer vision algorithms, and enables use of user device 220, and specifically an application hosted on user device 220, for second operator 210 dictation, image navigation, and markup. The user device 220 may meet particular privacy, security, and FDA requirements in such an application such that a smartphone is particularly well-suited to fulfill the requirements and provide the functionality described herein. In conventional systems, FDA-approved dictation devices were the only options available to users while the techniques described herein enables use of a wide variety of user devices, including smartphones. In particular, the AI system 218 aids the second operator 210 in producing high quality, image-rich, text-rich, and quick reports.

The report is subsequently stored in a database 214 and accessed by the operator 216. Conventional viewing systems for reports use text-only reports that are stored using a particular file extension. The systems described herein create image and text reports. The reports may still be viewable by conventional viewers by using a similar or compatible file extension, for backwards compatibility, such that the image and text reports are readily viewable by conventional viewing systems. The report, though including images in contrast to text-only previous reports, can be encoded as a JavaScript Object Notation ("JSON") object such that the report can be stored in a manner similar to conventional text-only reports. The encoding of the report enables the system to fit with existing databases 214 and does not require re-tooling or altering storage or access means for reports.

Figure 3:
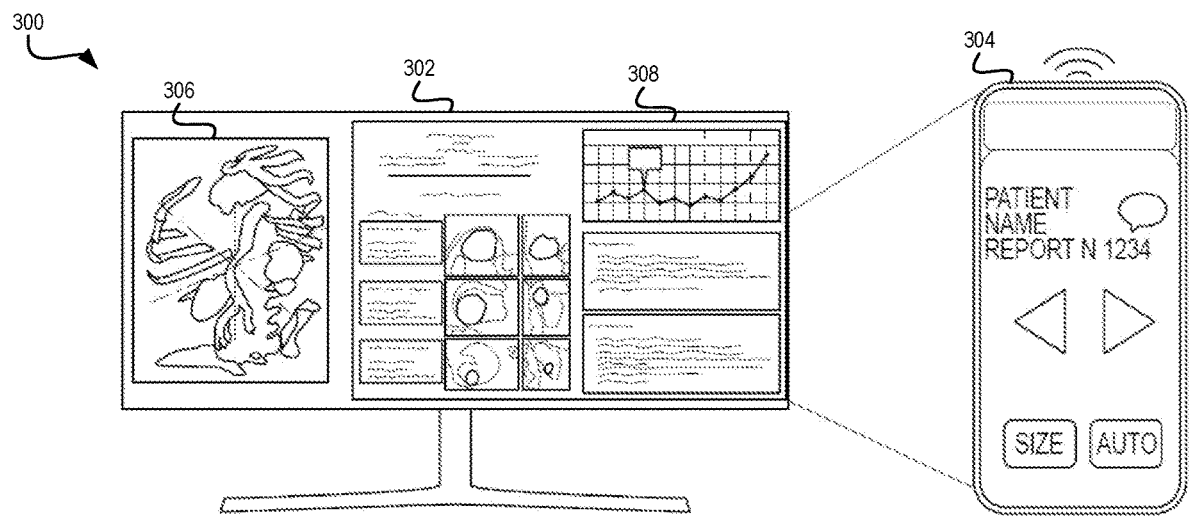
FIG. 3 illustrates an example report generation system for generating medical reports, according to at least some examples.

FIG. 3 illustrates an example report generation system 300 for generating medical reports, according to at least some examples. The report generation system 300 depicts elements of a system enabling a radiologist, such as second operator 210, to generate a medical report 308 based on medical images 306. The report generation system 300 includes a computing device having a display 302. The computing device may be a user device, such as the user device 402 described with respect to FIG. 4 including software and modules for performing methods associated therewith or, in some examples may be in communication with a remote computing device of the report generation system 300, such as the application server 404 of FIG. 4. The report generation system 300 also includes a mobile device 304 that is in communication with the computing device.

The mobile device 304 includes a microphone for speech input. Speech input to the mobile device is subsequently transcribed, by a transcription element, and processed with a natural language processing element. The report generation system 300 enables speech inputs from a second operator 210 to input notes for inclusion in the report as well as to instruct the report generation system 300 to include particular images from the image data 306. In some examples, the second operator 210 may input annotations into the image data 306 including notes, measurements, and other such notations through interaction with the display 302. The mobile device 304 may replace previous Dictaphones and provides additional capabilities in addition to speech input such as options to advance to a next patient or report; reviewing longitudinal studies and selecting computer vision algorithm results. The UI of the mobile device 304 provides additional flexibility over previous Dictaphones as buttons or elements of the UI may be configured with functionalities specific to each hospital or individual radiologists.

The report generation system 300 may, in some examples, automatically populate or include cropped images from the image data 306 in the report 308. The cropped images may be contextually cropped, as described with respect to FIG. 5. The cropped images may be accessed and included in the report 308 as a result of the report generation system 300 identifying that the second operator 210 is discussing a particular feature visible in the image data 306. In some examples, this may include processing the transcribed dictation from the second operator 210 and parsing references to particular anatomy. Computer vision algorithms of the report generation system may be implemented to identify anatomy or objects within the image data 306. The references to particular anatomy from the transcription are matched with identified anatomy or objects from the output of the computer vision algorithms. After identifying anatomy from the output of the computer vision algorithms, the report generation system 300 may crop the image data 306 around the identified anatomy and include the cropped image in the report 308.

In some examples, the report generation system 300 may additionally provide error-checking functions. For example by parsing, using the natural language processing algorithm, the information input into the report 308 and comparing against information obtained by using computer vision algorithms, errors such as incorrect references to anatomy (e.g., indicating a left leg has a particular medical issue while the computer vision algorithm only identifies an annotation, abnormality, or image data with respect to only a right leg of a patient). The error may be highlighted on the display 302 for the second operator 210 to correct or address in the report 308.

In an illustrative example, a second operator 210 measures a tumor within the image data 306 to include the measurements in the report 308. The measurements are included in the image data 308 as annotations identifying the object measured as well as the measurements taken. One or more computer vision algorithms then identifies a context preserving window within the image data 308 to crop. The crop around the tumor maintains the context of the tumor such that an operator 216 can subsequently view and understand the placement, orientation, size, shape, and other features of the tumor directly from the image data 306 included in the report 308. As the second operator 210 dictates or otherwise inputs their notes and comments into the report generation system 300, the report generation system identifies, based on natural language processing of the radiologists' notes, when the second operator 210 is discussing the tumor and automatically imports the cropped image into the report 308. The second operator 210 can subsequently edit the appearance, placement, or other features of the report 308 before storing the report 308 in a database for later access by an operator 216.

Figure 4:
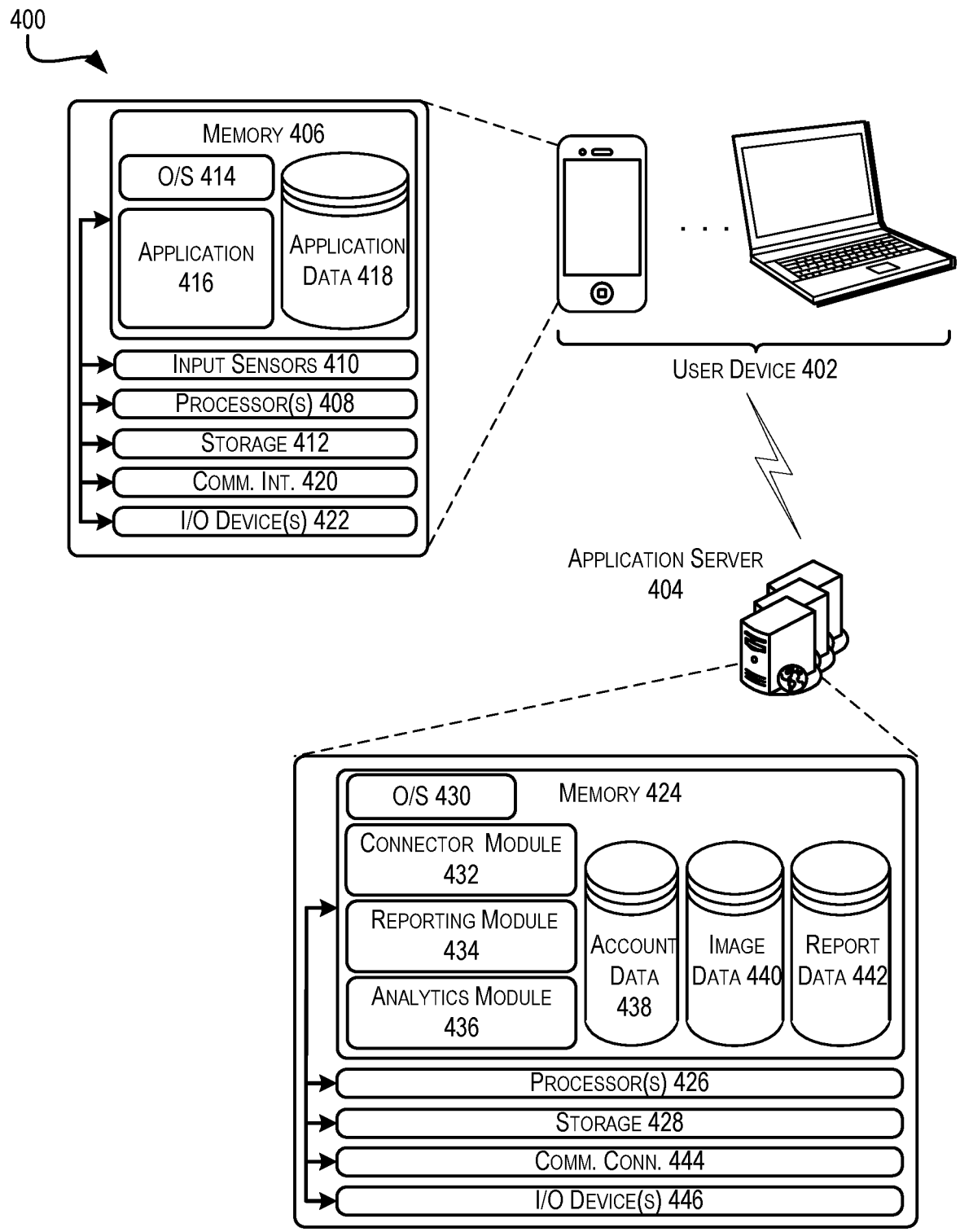
FIG. 4 illustrates an example system architecture for a system to generate medical reports, according to at least some examples.

FIG. 4 illustrates an example system architecture for a system 400 to generate medical reports, according to at least some examples. The system 400 may include the elements of the report generation system 300 described above. In FIG. 4, a user device 402 may be in communication with a number of other components, including at least an application server 404. The application server 404 may perform at least a portion of the processing functions of an application installed at the user device 402.

A user device 402 may be any suitable electronic device that is capable of providing at least a portion of the capabilities described herein. In particular, the user device 402 may be any electronic device capable of receiving data from a remote database and input devices, displaying information to a user, and outputting data to a database. In some embodiments, a user device 402 may be capable of establishing a communication session with another electronic device (e.g., application server 404 or mobile device 304) and transmitting/receiving data from that electronic device. A user device 402 may include the ability to download and/or execute applications. User devices 402 may include mobile communication devices as well as personal computers and thin-client devices. In some embodiments, a user device 402 may comprise any portable electronic device that has a primary function related to communication. For example, a user device 402 may be a smart phone, a personal data assistant (PDA), or any other suitable handheld device. The user device 402 can be implemented as a self-contained unit with various components (e.g., input sensors, one or more processors, memory, etc.) integrated into the user device 402. Reference in this disclosure to an "output" of a component or an "output" of a sensor does not necessarily imply that the output is transmitted outside of the user device 402. Outputs of various components might remain inside a self-contained unit that defines a user device 402.

In one illustrative configuration, the user device 402 may include at least one memory 406 and one or more processing units (or processor(s)) 408. The processor(s) 408 may be implemented as appropriate in hardware, computer-executable instructions, firmware or combinations thereof. Computer-executable instruction or firmware implementations of the processor(s) 408 may include computer-executable or machine executable instructions written in any suitable programming language to perform the various functions described. The user device 402 may also include one or more input sensors 410 for receiving user and/or environmental input such as speech input and user interactions with a user interface. There may be a variety of input sensors 410 capable of detecting user or environmental input, such as an accelerometer, a camera device, a depth sensor, a microphone, a global positioning system (e.g., GPS) receiver, etc.

The memory 406 may store program instructions that are loadable and executable on the processor(s) 408, as well as data generated during the execution of these programs. Depending on the configuration and type of user device 402, the memory 406 may be volatile (such as random access memory (RAM)) and/or non-volatile (such as read-only memory (ROM), flash memory, etc.). The user device 402 may also include additional storage 412, such as either removable storage or non-removable storage including, but not limited to, magnetic storage, optical disks, and/or tape storage. The disk drives and their associated computer-readable media may provide non-volatile storage of computer-readable instructions, data structures, program modules, and other data for the computing devices. In some implementations, the memory 406 may include multiple different types of memory, such as static random access memory (SRAM), dynamic random access memory (DRAM) or ROM. Turning to the contents of the memory 406 in more detail, the memory 406 may include an operating system 414 and one or more application programs or services for implementing the features disclosed herein including at least an application 416. The memory 406 may also include application data 418, which provides information to be generated by and/or consumed by the application 416. In some embodiments, the application data 418 may be stored in a database.

For the purposes of this disclosure, an application 416 may be any set of computer executable instructions installed upon, and executed from, a user device 402. Application 416 may be installed on a user device 402 by a manufacturer of the user device 402 or by another entity. In some embodiments, the application 416 may cause a user device 402 to establish a communication session with an application server 404 that provides backend support for the application 416. An application server 404 may maintain account information associated with a particular user device 402 and/or user. In some embodiments, a user may be required to log into an application 416 in order to access functionality provided by the application 416.

In accordance with at least some embodiments, the application 416 may be configured to provide a GUI enabling generation of a medical report as well as providing contextual image cropping of medical images in accordance with the methods described herein. In accordance with at least some embodiments, the application 416 may receive output from the input sensors 410 and identify speech, user interactions, annotations, or potential objects within that output. For example, the application 416 may input speech from a microphone, such as the microphone previously described with respect to input sensors 410. Based on this information, the application 416 may enable transcription of the speech input and generate report information based on the speech input. For example, speech input may include notes to be transcribed and included in a report as well as instructions to include a particular subset of image data in the report. In another example, the application 416 may utilize one or more computer vision algorithms to identify anatomy within the medical images and identify a window to crop the image data that preserves the anatomy as well as a surrounding context of the anatomy. In this example, the application 416 may receive image information from an image database 440 of the application server 404 and annotations or user inputs through input sensors 410 as the user interacts with the image data. In some embodiments, the application 416 may cause the user device 402 to transmit the output obtained from the input sensors 410 to the application server 204, which may then perform one or more natural language processing techniques or computer vision techniques upon that output for respective speech input or user inputs related to the image data.

The user device 402 may also contain communications interface(s) 420 that enable the user device 402 to communicate with any other suitable electronic devices. In some examples, the user device 402 may include multiple user devices 402 in communication with one another, such as a personal computer and a mobile device in communication with one another. In some examples, the communication interface 420 may enable the user device 402 to communicate with other electronic devices on a network (e.g., on a private network). For example, the user device 402 may include a Bluetooth wireless communication module, which allows it to communicate with another electronic device (e.g., a Bluetooth laser measuring tape, etc.). The user device 402 may also include input/output (I/O) device(s) and/or ports 422, such as for enabling connection with a keyboard, a mouse, a pen, a voice input device, a touch input device, a display, speakers, a printer, etc.

In some embodiments, the user device 402 may communicate with the application server 404 via a communication network. The communication network may include any one or a combination of many different types of networks, such as cable networks, the Internet, wireless networks, cellular networks, and other private and/or public networks. In addition, the communication network may comprise multiple different networks. For example, the user device 402 may utilize a wireless local area network ("WLAN") to communicate with a wireless router, which may then route the communication over a public network (e.g., the Internet) to the application server 404.

The application server 404 may be any computing device or plurality of computing devices configured to perform one or more calculations on behalf of the application 416 on the user device 402. In some embodiments, the application 416 may be in periodic communication with the application server 404. For example, the application 416 may receive updates, push notifications, or other instructions from the application server 404. In some embodiments, the application 416 and application server 404 may utilize a proprietary encryption and/or decryption scheme to secure communications between the two. In some embodiments, the application server 404 may be executed by one or more virtual machines implemented in a hosted computing environment. The hosted computing environment may include one or more rapidly provisioned and released computing resources, which computing resources may include computing, networking, and/or storage devices. A hosted computing environment may also be referred to as a cloud-computing environment.

In one illustrative configuration, the application server 404 may include at least one memory 424 and one or more processing units (or processor(s)) 426. The processor(s) 426 may be implemented as appropriate in hardware, computer-executable instructions, firmware or combinations thereof. Computer-executable instruction or firmware implementations of the processor(s) 426 may include computer-executable or machine executable instructions written in any suitable programming language to perform the various functions described.

The memory 424 may store program instructions that are loadable and executable on the processor(s) 426, as well as data generated during the execution of these programs. Depending on the configuration and type of application server 404, the memory 424 may be volatile (such as random access memory (RAM)) and/or non-volatile (such as read-only memory (ROM), flash memory, etc.). The application server 404 may also include additional storage 428, such as either removable storage or non-removable storage including, but not limited to, magnetic storage, optical disks, and/or tape storage. The disk drives and their associated computer-readable media may provide non-volatile storage of computer-readable instructions, data structures, program modules, and other data for the computing devices. In some implementations, the memory 424 may include multiple different types of memory, such as static random access memory (SRAM), dynamic random access memory (DRAM) or ROM.

Turning to the contents of the memory 424 in more detail, the memory 424 may include an operating system 430 and one or more application programs or services for implementing the features disclosed herein including at least a module for receiving image data and outputting or encoding a report for output (connector module 432) and/or a module for producing expressive reports that include text, images, tables, measurements, and other such data (reporting module 434) and/or a module for advanced language, speech, and image analysis services (analytics module 436). The memory 424 may also include account data 438, which provides information associated with user accounts maintained by the described system, image data 440, which includes medical image data gathered and stored from medical imaging devices, and/or report data 442, which stores and provides information on a number of reports including completed reports and pending reports. In some embodiments, one or more of the account data 438, the image data 440, or the report data 442 may be stored in a database.

The memory 424, memory 406, and the additional storage 428, both removable and non-removable, are examples of computer-readable storage media. For example, computer-readable storage media may include volatile or non-volatile, removable or non-removable media implemented in any method or technology for storage of information such as computer-readable instructions, data structures, program modules or other data. As used herein, the term "modules" may refer to programming modules executed by computing systems (e.g., processors) that are installed on and/or executed from the application server 404. The application server 404 may also contain communications connection(s) 444 that allow the application server 404 to communicate with a stored database, another computing device or server, user terminals, and/or other components of the described system. The application server 404 may also include input/output (I/O) device(s) and/or ports 446, such as for enabling connection with a keyboard, a mouse, a pen, a voice input device, a touch input device, a display, speakers, a printer, etc.

Turning to the contents of the memory 424 in more detail, the memory 424 may include the connector module 432, the reporting module 434, the analytics module 436, the database containing account data 438, the database containing image data 440, and/or the database containing report data 442.

In some embodiments, the connector module 432 may be configured to, in conjunction with the processor(s) 426, receive image data from the image data 440, receive input sensor data from the user device 402, and output reports to report data 442. The connector module 432 is interoperable between various systems and databases according to Digital Imaging and Communication in Medicine ("DICOM®") and Health Level 7 ("HL7") which provide frameworks and related standards for the exchange, integration, sharing, and retrieval of electronic health data. The connector module 432 may output the report into any suitable format accessible by operators, for example including a JSON format such that embedded images within the report may be encoded to be compatible with existing systems that may typically only provide viewing of text-only reports.

In some embodiments, the reporting module 434 may be configured to, in conjunction with the processor(s) 426, receive, edit, and produce reports including text, images, tables, and measurements. The reporting module 434 may interface with third party viewers, such as web-based image viewers and editing software. The reporting module 434 receives inputs from the input sensors 410 as well as the analytics module 436 and image data 440 to generate a report. The reporting module 434 interfaces with the connector module 432 to receive as well as output information to various systems and databases.

In some embodiments, the analytics module 436 may be configured to, in conjunction with the processor(s), provide language, speech, and image analysis for use by the reporting module and access by the user via the user device 402 in generating the report. The analytics module 436 may, in some embodiments, be configured to provide image cropping in accordance with methods described herein. The analytics module 436 may provide speech transcription, image classification, anatomy localization, vertebrae localization and labeling, image alignment, interactive segmentation and measurement of anatomy, among other speech, text, and image analysis processing.

The analytics module 436 provides speech-to-text transcription to transform speech input data received through input sensor 410 into text. In some embodiments, the analytics module 436 may interface with external transcription services, including transcription services optimized for medical applications. In some embodiments, the analytics module 436 may include a machine learning algorithm trained using medical terminology to transcribe speech input into text data. The analytics module may further include natural language processing algorithm(s) to determine medical terms, entities, relations, ontologies, in addition to determining natural language recognition capable of identifying imperative commands, such as commands from the user instructing the reporting module 434 to generate, revise, edit, or produce at least a portion of a medical report. In some examples, the analytics module may provide utterance understanding and perform actions, or cause the processor 426 to perform actions based on speech input and parse report data from imperative commands to transcribe and incorporate transcribed report data into the report without any particular indication by the user. In such examples, the user may dictate a string of information such as describing a particular abnormality in the image data and in the string include an imperative command to include a cropped image of the abnormality.

The analytics module 436 additionally provides computer vision algorithms to focus on detection of anatomy and abnormalities. The computer vision algorithms may focus on general tasks including detection of anatomy and abnormalities and may also include specific computer vision algorithms for detecting or identifying disease-specific tasks (such as detecting particular tumors). In some examples, the analytics module 436 may include an image segmentation algorithm for interactive delineation and measurement of any generic structure of interest in two- and three-dimensions. Image segmentation algorithms may also compute and report volumes and linear measurements according to user interactions with the GUI. The analytics module may also include an image modality classification algorithm that recognizes a modality of the medical images (e.g., CT, CT angiogram, MR T1, MR T2, MR T1-contrast, MR and FLAIR). The modality classification information may be included in the report and may also be used to select a particular computer vision algorithm for performing relevant measurements and detection. The analytics module 436 may include an anatomical view classification that recognizes a viewed anatomical region within the image data. The anatomical view classification may be useful for further identifying specific organs and additional anatomy within the image data and may also be useful for selecting further computer vision algorithms. The analytics module 436 may also include an organ localization algorithm that generated bounding boxes around organs within the image data. Examples of bounding boxes output by the organ localization algorithm are depicted with respect to FIG. 6. The analytics module 436 may also include a vertebrae labeling algorithm that detects each vertebra in image data and names the vertebra according to the standard anatomical naming convention for vertebrae. The analytics module 436 may also include a study alignment algorithm that registers and maps image data gathered at different points in time for comparison of a particular portion of the patient over a period of time, for example to track the progression of treatment. The analytics module 436 may also include an anomaly segmentation algorithm which localizes and segments generic anomalies in image data. The anomaly segmentation algorithm may enable detection and identification of anomalies without specific diagnosis of the type of abnormality, as such a determination is readily made by a radiologist. In some examples, the analytics module 436 may include additional algorithms including computer vision algorithms, language processing algorithms, and other such algorithms for processing image, speech, text, and other data.

Figure 5:
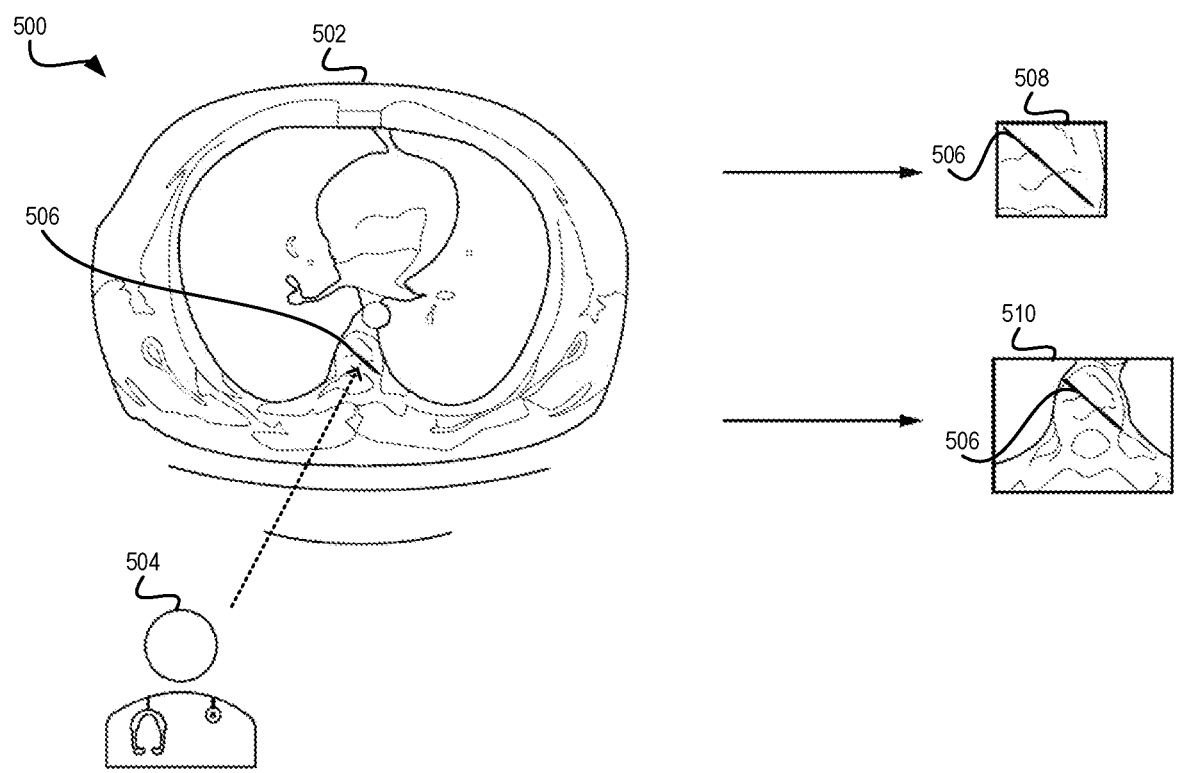
FIG. 5 illustrates an example of a medical image including an annotation and a resulting crop according to a conventional system as well as a contextually aware system, according to at least some examples.

FIG. 5 illustrates an example 500 of a medical image 502 including an annotation 506 and a resulting crop 508 according to a conventional system as well as a crop 510 as a result of contextually aware system, according to at least some examples. In the medical image 502, an annotation 506 is placed by a user 504. The annotation 506 may include a measurement as shown and may also include additional information such as a volume of the identified anatomy as determined by a computer vision algorithm or user-input notes. Crop 508 includes the annotation 506 but does not include a surrounding context, which makes the crop 508 less useful to an operator than crop 510, which includes a surrounding context. Crop 510 may be determined by the analytics module 436 and presented at the GUI of user device 402.

The surrounding context around the annotation may be selected or identified in any number of ways. In a first example, the systems described herein may generate the crop 510 by defining a window that is a certain percentage larger than the dimensions of the annotation itself. For instance, the annotation 506 may traverse a first width and a first height within the medical image 502 and the crop 510 may be determined as a factor of the first width and the first height. In some examples the crop 510 may have a second width and a second height that are each fifty percent larger than the first width and the first height, respectively. In some examples the second width and second height may be more or less than fifty percent larger than the first width and the second width.

In some examples, the crop 510 may be determined based on object detection by one or more computer vision algorithms of the analytics module 436. For example, an object classifier algorithm of the analytics module 436 may be used to determine crop 436. While object detectors are specialized for one object class, such as cars or swans, the object classifier algorithm may be trained to measure an "objectness" over various classes of objects. For example, the object classifier algorithm may quantify how likely it is for an image window or crop window to cover an object of any class. Objects are standalone things with a well-defined boundary and center, in contrast to background or surrounding environment. In some examples, the crop 510 may be determined within the medical image 502 by first identifying a location of the annotation 506 within the medical image 502. The object classifier algorithm described above may then be performed in an area including the annotation 506.

In some examples, the crop 510 may be identified and cropped from the medical image 502 based on the assumption that objects within a medical image are often standalone items with well-defined closed boundaries and centers. As such, generic objects with well-defined closed boundaries share surprisingly strong correlation in terms of the norm of their gradients after resizing their corresponding image windows to a small fixed size (e.g., 8×8 pixels). In an example process, a medical image 502 or portion thereof is resized to a particular small fixed size and the norm of the gradients within the small image is used to identify objects with closed, well-defined boundaries. The window for crop 510 may then be applied to the medical image 510 such that the window does not cross a gradient within the medical image 502 or the small image. Since objects have well-defined, closed boundaries, by ensuring the window for crop 510 does not cross any gradients, objects associated with annotation 506 will be fully enclosed within crop 510.

Figure 6:
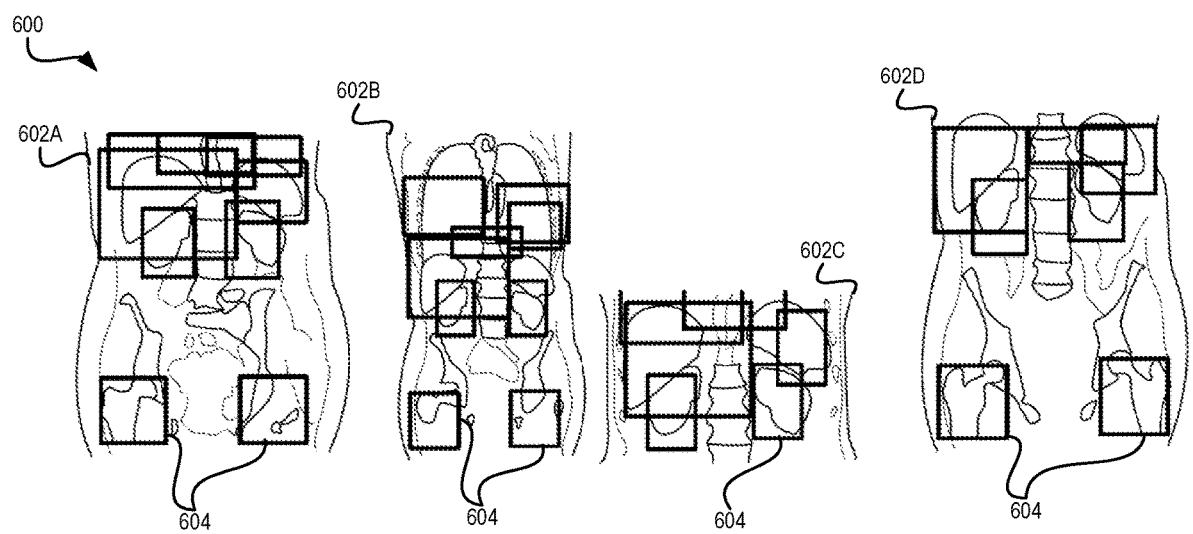
FIG. 6 illustrates examples of medical images with detected anatomy using computer vision algorithms, according to at least some examples.

FIG. 6 illustrates examples of medical images 602A-D with detected anatomy using computer vision algorithms, according to at least some examples. The medical images 602A-D have bounding boxes 604 identifying major anatomical structures (i.e., lungs, liver, spleen, kidneys, and femurs). The bounding boxes are generated and placed in the medical images 602A-D by a computer vision algorithm, such as an organ localization algorithm of the analytics module 436. Once particular organs or anatomical structures have been identified with bounding boxes 604, windows for crop 510 may be located and sized based on the bounding boxes 604, for example by ensuring the bounding box 604 is entirely enclosed within the crop 510 or by sizing the crop 510 to a multiple of the dimensions of the bounding box 604 and co-locating the centers of the bounding box 604 and crop 510. Additionally, during report generation, an error-checking function of the report generation system 300 may use the data corresponding to identified and localized organs within bounding boxes 604 to ensure the contents of the report are entered correctly.

In some examples, the computer vision algorithm may analyze the medical images 602A-D in conjunction with analysis by a user. The computer vision algorithms may identify potential areas of interest and generate a list or notification for the user of potentially identified areas of interest to aid the analysis by the user. The computer vision algorithms can, in this manner, enhance the analytical abilities and skills of the user as they make informed decisions and identification of items within the medical images 602A-D. In some examples, after the user has made a particular annotation or observation, the computer vision algorithms may identify similar features within the medical images 602A-D, or features similar to those annotated by the user.

In an example, the computer vision algorithm may initially identify an input with respect to one or more features or anatomy of the patient. A similarity between the received input and other features visible within the image data may be identified by the computer vision algorithm. The similarity may be based on the organ identity, location of the organ, location of another organ, a separate organ or anatomical feature, and different medical condition shown in the image data. In some examples, the computer vision algorithm may provide a list of suggestions in an order based on a ranking provided by a confidence score output by the computer vision algorithm and one or more algorithms, such as a machine learning algorithm enabling identification of anatomical features in image data.

In an example, the computer vision algorithm may not identify a particular similarity, as described above. The computer vision algorithm may, in some examples, detect additional features in the image data. As the user discusses one of the features identified by the computer vision algorithm, the computer vision algorithm may provide, to the user, a list of additional features visible in the image data, for example for enable the user to easily verify that they have discussed any other relevant features besides the presently discussed feature.

Figure 7:
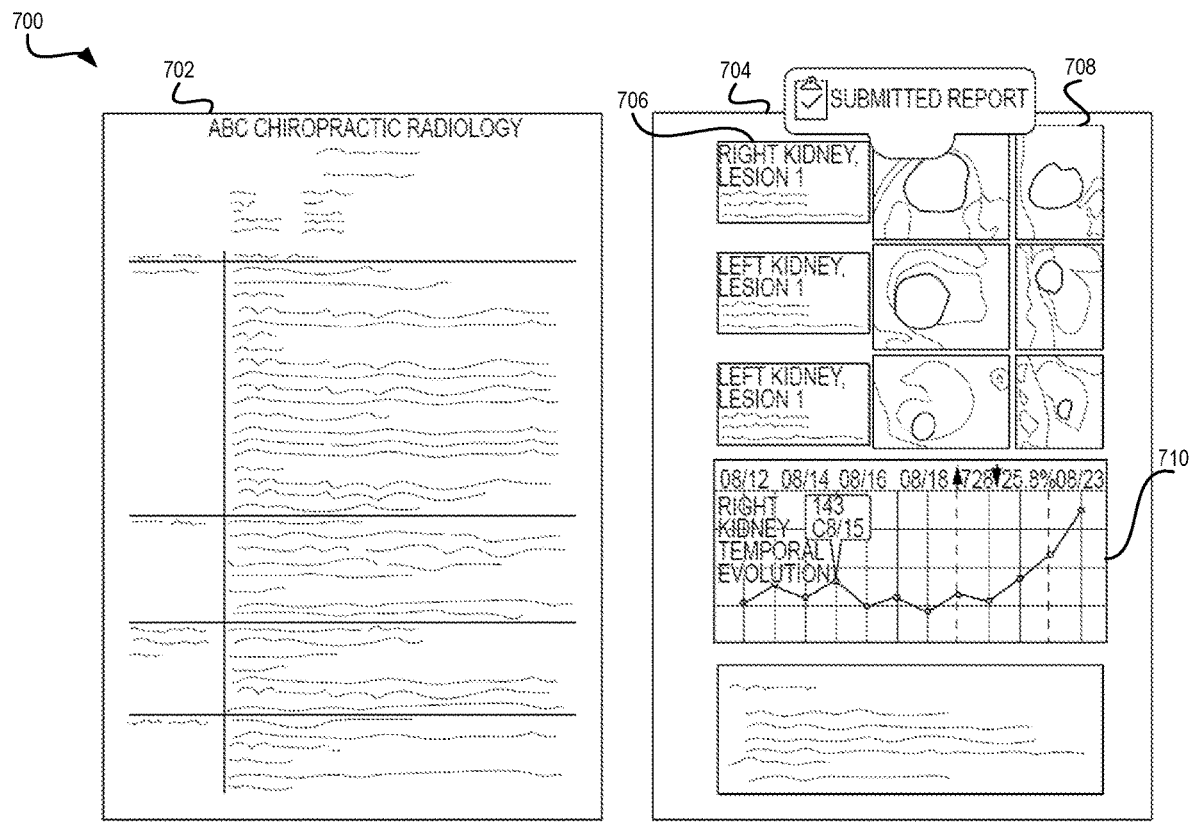
FIG. 7 illustrates a side by side example of a conventional medical report and a medical report generated using a report generation system with contextual image cropping, according to at least some examples.

FIG. 7 illustrates a side by side example of a conventional medical report 702 and a medical report 704 generated using a report generation system 300 with contextual image cropping, according to at least some examples. Conventional medical reports 702 are text-only and do not provide high-quality information for ease of operator use in determining treatment for a patient. The conventional medical report 702 report is text only, and provides no quantification of the clinical issue, nor rigorous comparison to previous studies. This lack of precise visualizations and quantitative information may result in clinical issues. For example, in a text-only report a kidney surgeon would not be able to understand the shape of a tumor, or if it is close to an artery.

The medical report 704, includes text 706 that is augmented by images 708, which may have been automatically populated from crops 510 by a report generation system as described herein. Charts 710 and additional data may also be included within the medical report 704. Information such as images 708 and charts 710 in addition to text 706 is crucial to the downstream operators and provide needed context and information not otherwise readily available to an operator.

Figure 8:
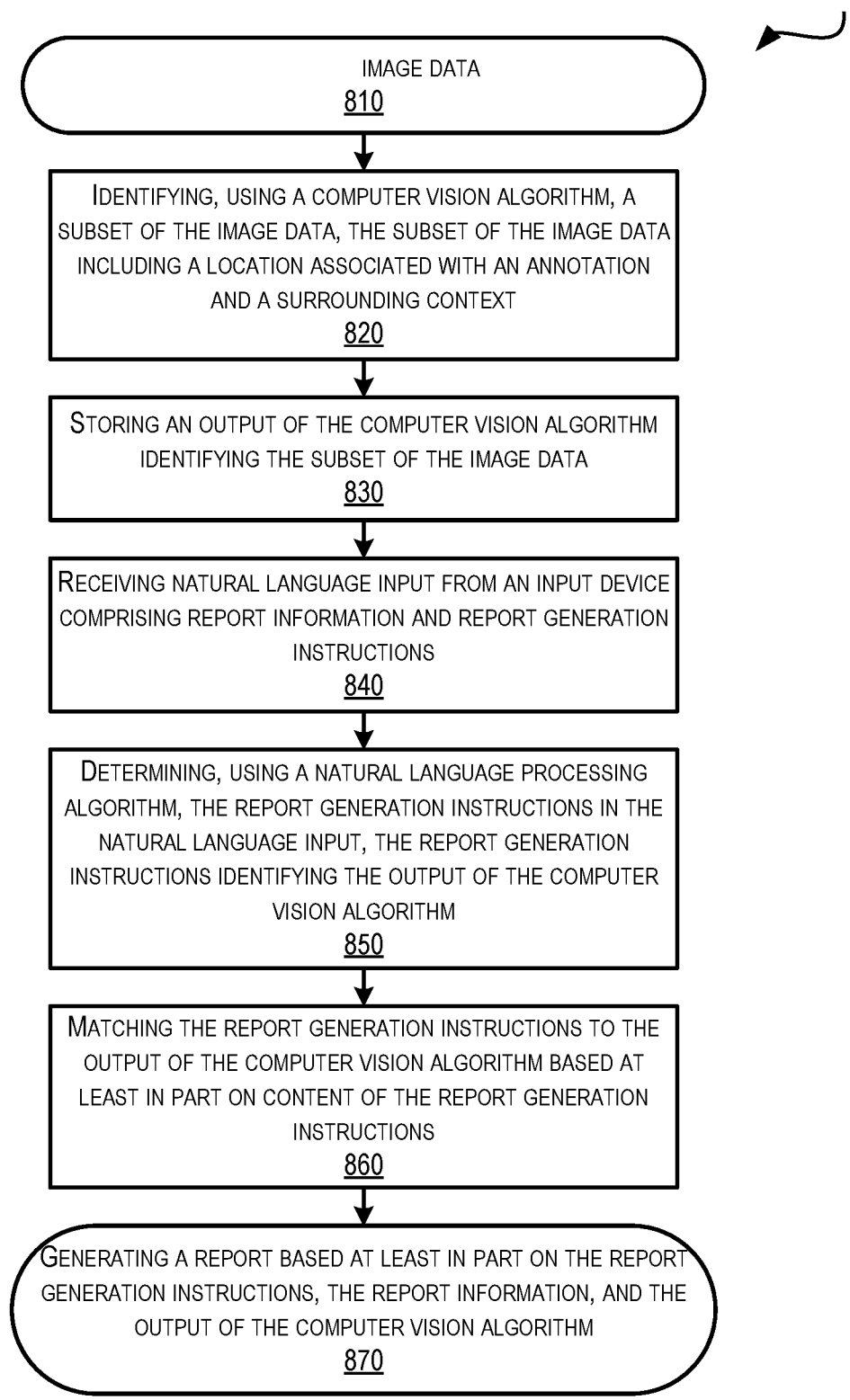
FIG. 8 is a flow diagram illustrating an example process for generating medical reports, according to at least some examples.

FIG. 8 is a flow diagram illustrating an example process 800 for generating medical reports, according to at least some examples. Some or all of the process 800 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

At 810, the process 800 includes receiving image data. The image data may be medical imaging data, for example as gathered by a medical imaging device, such as an x-ray, MRI, or CT machine. In some examples, the image data may be received at a computing device configured to perform methods described herein. In some examples, the image data may be received from a database, such as image data 440. In some examples, receiving the image data includes requesting image data corresponding to a particular patient, or accessing the database including image data for a particular patient.

At 820, the process 800 includes identifying, using a computer vision algorithm, a subset of the image data, the subset of the image data including a location associated with an annotation and a surrounding context. The computer vision algorithm may be a computer vision algorithm of the analytics module 436 and may identify an object, anatomy, anomaly, or any subset of the image data. In particular, an annotation included within the image data, such as an annotation placed by a radiologist, may enable selection of a subset of the image data including the annotation.

In some examples, the computer vision algorithm may be triggered or initialized to begin analysis on the image data based on speech data from the user. For example, the computer vision algorithm may not identify any portion of the image data or perform any operations until initialized by the user. For example, the user may dictate to the system that the user is focusing their attention on or begin describing features of a particular organ visible in the image data. The system may initialize the computer vision algorithm based on identifying that the user is discussing the organ, and perform one or more operations with the computer vision algorithm on the identified organ or in the image data generally.

In some examples, selecting the subset of the image data includes cropping the image data, or determining a size and location for a crop window within the image data. The crop window may be positioned within the image data such that the annotation falls entirely within the crop window. Furthermore, the crop window may have dimensions that provide for surrounding image data to be included within the crop window surrounding the annotation. For instance, the crop window may be sized based on encompassing an object associated with a location of the annotation within the image data, for example as described with respect to FIG. 5.

At 830, the process 800 includes storing an output of the computer vision algorithm identifying the subset of the image data. The output of the computer vision algorithm may include the crop window, the subset of the image data, identities and locations of objects, organs, anomalies, or any other data produced by computer vision algorithms. The output of the computer vision algorithm may be stored as data associated with the image data or may be stored independently of the image data. The output of the computer vision algorithm may be stored in a local memory or in a remote memory of an application server. The output may be accessible to a user of a report generation system for generating a medical report.

At 840, the process 800 includes receiving natural language input from an input device comprising report information and report generation instructions. The natural language input may include speech or text input through an input device such as a microphone or keyboard of a computing device, such as a computer or mobile device. The natural language input may include dictated notes from a radiologist relating to the image data such as the report information. The natural language input may also include imperative statements corresponding to instructions for generating a medical report, for example "include image of XYZ here." In some examples only report information may be received by the input device and report generation instructions may be generated based solely on the content of the report information. For instance, while discussing a particular tumor, report generation instructions may be produced by the system itself instructing placement of an image of the tumor within the report.

At 850, the process 800 includes determining, using a natural language processing algorithm, the report generation instructions in the natural language input, the report generation instructions identifying the output of the computer vision algorithm. A natural language processing algorithm of the analytics module 436 may enable processing of the natural language input and may parse out the report information and the report generation instructions, for example by identifying imperative statements or instructions for placement of images within the natural language input. As described above with respect to 840, the report generation instructions may not include imperative statements but may be produced by the system in response to identifying, using the natural language algorithm, that the radiologist is discussing a particular object or output of the computer vision algorithm.

At 860, the process 800 includes matching the report generation instructions to the output of the computer vision algorithm based at least in part on content of the report generation instructions. Matching the instructions to the output may include identifying an item or object mentioned in the report information or report generation instructions and identifying a corresponding element within the outputs of one or more computer vision algorithms of the analytics module 436.

At 870, the process 800 includes generating a report based at least in part on the report generation instructions, the report information, and the output of the computer vision algorithm. The report may be automatically generated by the system according to the report information and the report generation instructions. The report includes the report information and output of the computer vision algorithm, such as a crop of the image data with an annotation therein. The report may be compiled and output or exported in any suitable format, such as JSON.

In some examples, generating the report may also include providing, through the GUI, proofreading and error-checking capabilities for the report as it is generated in real-time. For example, the error-checking may be performed by parsing, using the natural language processing algorithm, the information input into the report by the operator and comparing the information that is input against information obtained by using computer vision algorithms. After performing the comparison, errors such as incorrect references to anatomy (e.g., indicating a left leg has a particular medical issue while the computer vision algorithm only identifies an annotation, abnormality, or image data with respect to only a right leg of a patient) may be identified if present by identifying apparent mismatches in discussion within a report and identification of the discussed anatomy in the output of the computer vision algorithms. The error may be highlighted on the display for the operator to correct or address in the report.

Figure 9:
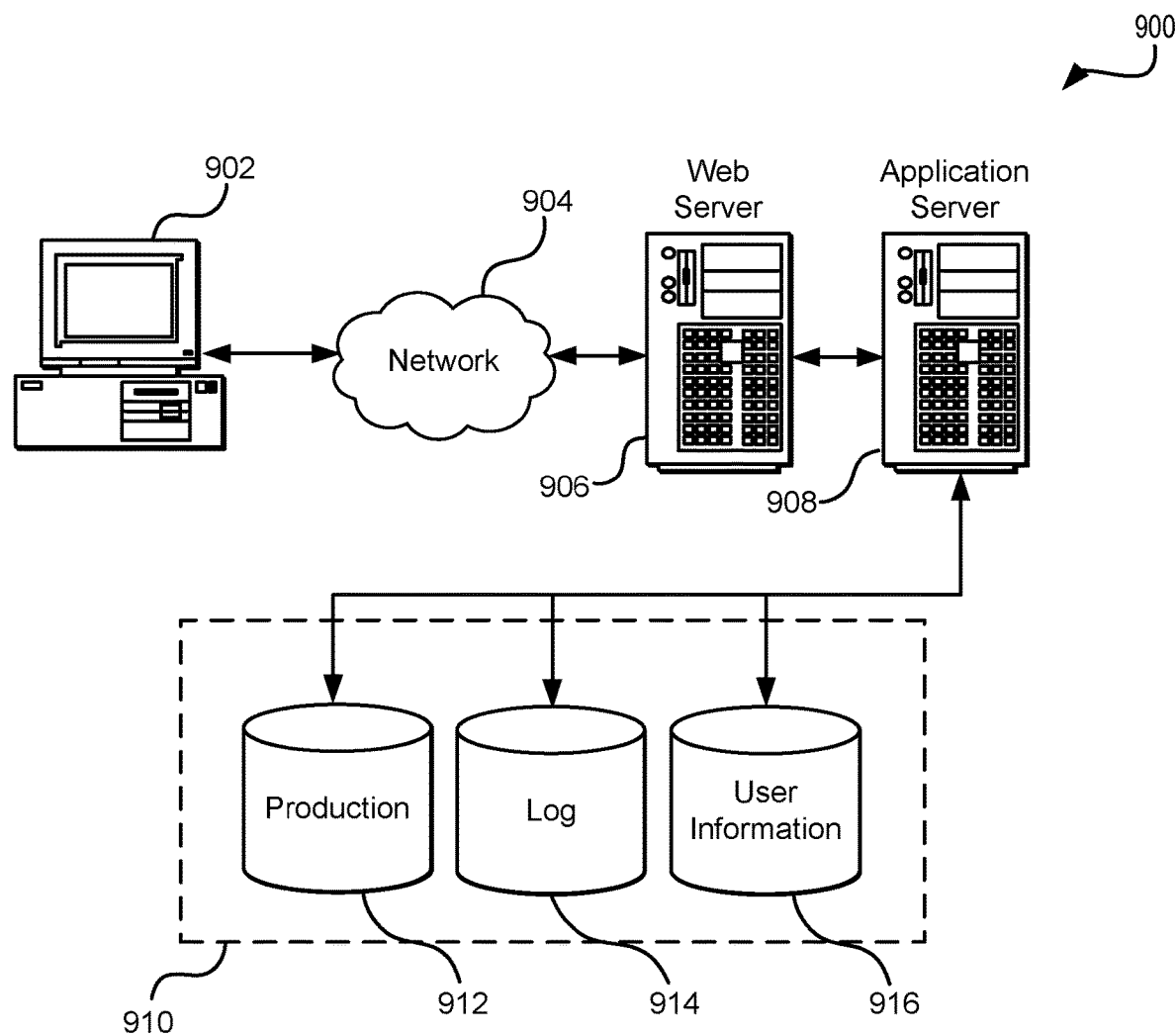
FIG. 9 illustrates an environment in which various embodiments can be implemented.

FIG. 9 illustrates aspects of an example environment 900 for implementing aspects in accordance with various embodiments. As will be appreciated, although a Web-based environment is used for purposes of explanation, different environments may be used, as appropriate, to implement various embodiments. The environment includes an electronic client device 902, which can include any appropriate device operable to send and receive requests, messages, or information over an appropriate network 904 and convey information back to a user of the device. Examples of such client devices include personal computers, cell phones, handheld messaging devices, laptop computers, set-top boxes, personal data assistants, electronic book readers, and the like. The network can include any appropriate network, including an intranet, the Internet, a cellular network, a local area network, or any other such network or combination thereof. Components used for such a system can depend at least in part upon the type of network and/or environment selected. Protocols and components for communicating via such a network are well known and will not be discussed herein in detail. Communication over the network can be enabled by wired or wireless connections and combinations thereof. In this example, the network includes the Internet, as the environment includes a Web server 906 for receiving requests and serving content in response thereto, although for other networks an alternative device serving a similar purpose could be used as would be apparent to one of ordinary skill in the art.

The illustrative environment includes at least one application server 908 and a data store 910. It should be understood that there can be several application servers, layers, or other elements, processes, or components, which may be chained or otherwise configured, which can interact to perform tasks such as obtaining data from an appropriate data store. As used herein the term "data store" refers to any device or combination of devices capable of storing, accessing, and retrieving data, which may include any combination and number of data servers, databases, data storage devices, and data storage media, in any standard, distributed, or clustered environment. The application server can include any appropriate hardware and software for integrating with the data store as needed to execute aspects of one or more applications for the client device, handling a majority of the data access and business logic for an application. The application server provides access control services in cooperation with the data store and is able to generate content such as text, graphics, audio, and/or video to be transferred to the user, which may be served to the user by the Web server in the form of HyperText Markup Language ("HTML"), Extensible Markup Language ("XML"), or another appropriate structured language in this example. The handling of all requests and responses, as well as the delivery of content between the client device 902 and the application server 908, can be handled by the Web server. It should be understood that the Web and application servers are not required and are merely example components, as structured code discussed herein can be executed on any appropriate device or host machine as discussed elsewhere herein.

The data store 910 can include several separate data tables, databases or other data storage mechanisms and media for storing data relating to a particular aspect. For example, the data store illustrated includes mechanisms for storing production data 912 and user information 916, which can be used to serve content for the production side. The data store also is shown to include a mechanism for storing log data 914, which can be used for reporting, analysis, or other such purposes. It should be understood that there can be many other aspects that may need to be stored in the data store, such as for page image information and to access right information, which can be stored in any of the above listed mechanisms as appropriate or in additional mechanisms in the data store 910. The data store 910 is operable, through logic associated therewith, to receive instructions from the application server 908 and obtain, update or otherwise process data in response thereto. In one example, a user might submit a search request for a certain type of item. In this case, the data store might access the user information to verify the identity of the user and can access the catalog detail information to obtain information about items of that type. The information then can be returned to the user, such as in a results listing on a Web page that the user is able to view via a browser on the user device 902. Information for a particular item of interest can be viewed in a dedicated page or window of the browser.

Each server typically will include an operating system that provides executable program instructions for the general administration and operation of that server and typically will include a computer-readable storage medium (e.g., a hard disk, random access memory, read only memory, etc.) storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 9. Thus, the depiction of the system 900 in FIG. 9 should be taken as being illustrative in nature and not limiting to the scope of the disclosure.

The various embodiments further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most embodiments utilize at least one network that would be familiar to those skilled in the art for supporting communications using any of a variety of commercially-available protocols, such as Transmission Control Protocol/Internet Protocol ("TCP/IP"), Open System Interconnection ("OSI"), File Transfer Protocol ("FTP"), Universal Plug and Play ("UpnP"), Network File System ("NFS"), Common Internet File System ("CIFS"), and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a Web server, the Web server can run any of a variety of server or mid-tier applications, including Hypertext Transfer Protocol ("HTTP") servers, FTP servers, Common Gateway Interface ("CGI") servers, data servers, Java servers, and business application servers. The server(s) also may be capable of executing programs or scripts in response to requests from user devices, such as by executing one or more Web applications that may be implemented as one or more scripts or programs written in any programming language, such as Java©, C, C#, or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit ("CPU"), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired)), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, Electrically Erasable Programmable Read-Only Memory ("EEPROM"), flash memory or other memory technology, Compact Disc Read-Only Memory ("CD-ROM"), digital versatile disk (DVD), or other optical storage, magnetic cassettes, magnetic tape, magnetic disk storage, or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions, and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system comprising:
one or more processors; and one or more non-transitory computer-readable media having instructions stored thereon that, when executed by the one or more processors, cause the system to:
receive radiology image data for a radiological image of a patient and a medical annotation associated with the radiology image of the patient;
identify, using a computer vision algorithm, an annotated portion of the radiology image of the patient corresponding to the medical annotation, the annotated portion of the radiology image of the patient excluding a portion of the radiology image of the patient surrounding a cropping window;
store an output of the computer vision algorithm, the output identifying the annotated portion of the radiology image of the patient;
receive speech input from an input device, the speech input comprising medical notes for the patient and report generation instructions for a medical report for the patient;
identify, using a natural language processing algorithm, an instruction in the speech input, the instruction comprising the report generation instructions and identifying an anatomical feature of the patient;
determine whether an image of the anatomical feature of the patient is included in the annotated portion of the radiology image of the patient; and
in response to determining that the image of the anatomical feature of the patient is included in the annotated portion of the radiology image of the patient, generate an image-based radiology report according to the instruction by including the image of the anatomical feature of the patient, the medical notes, and the medical annotation into the image-based radiology report.

2. The system of claim 1, wherein identifying the annotated portion of the radiology image of the patient comprises determining the cropping window that the cropping window does not cross a gradient within the radiology image of the patient.

3. A method implemented on a computing device, comprising:
receiving medical diagnostic image data for a diagnostic image of a patient;
identifying, using a computer vision algorithm, an annotated portion of the diagnostic image of the patient, wherein the annotated portion comprises a first portion of the diagnostic image associated with an annotation and a second portion of the diagnostic image that surrounds the first portion, and wherein the second portion is selected to illustrate location of the first portion within the diagnostic image of the patient;
storing an output of the computer vision algorithm identifying the annotated portion of the diagnostic image;
receiving natural language input from an input device comprising report information and report generation instructions that identify an anatomical feature of the patient;
identifying, using a natural language processing algorithm, the report information and the report generation instructions in the natural language input;
determining whether an image of the anatomical feature is included in the annotated portion of the diagnostic image; and
in response to determining that the image of the anatomical feature is included in the annotated portion of the diagnostic image, generating a medical report for the patient that comprises the annotated portion of the diagnostic image and the report information.

4. The method of claim 3, further comprising generating an error notification in response to determining that the anatomical feature is not included in the annotated portion of the diagnostic image.

5. The method of claim 4, wherein the error notification indicates that the annotated portion of the diagnostic image does not include an image of the anatomical feature.

6. The method of claim 3, wherein the natural language input is received based at least in part on audio detected by a microphone of the input device, and wherein the natural language input comprises dictated information comprising the report information and the report generation instructions.

7. The method of claim 3, wherein identifying, using the computer vision algorithm, the annotated portion of the diagnostic image is based on the natural language input.

8. The method of claim 3, wherein the output of the computer vision algorithm is stored as a JavaScript Object Notation (JSON) file; and
further comprising generating the medical report comprises encoding the annotated portion of the diagnostic image and the report information as JSON objects.

9. The method of claim 3, wherein identifying the annotated portion of the diagnostic image comprises determining a cropping window that does not cross a gradient within-the diagnostic image and cropping the diagnostic image using the cropping window.

10. The method of claim 3, wherein identifying the annotated portion of the diagnostic image comprises selecting the computer vision algorithm from a set of computer vision algorithms based at least in part on the annotation.

11. The method of claim 10, wherein the set of computer vision algorithms comprise at least one of:
an image segmentation algorithm;
a speech transcription algorithm;
a modality classification algorithm;
an anatomy view classification algorithm;
an organ localization algorithm;
a vertebrae labelling algorithm;
a study alignment algorithm; and
an anomaly segmentation algorithm.

12. The method of claim 3, wherein identifying the annotated portion of the diagnostic image comprises determining a cropping window surrounding an object associated with the annotation and identified by the computer vision algorithm, the cropping window shaped and positioned such that a perimeter of the cropping window does not cross a gradient within the diagnostic image.

13. The method of claim 3, wherein generating the medical report is based at least in part on the report generation instructions comprising inserting the annotated portion of the diagnostic image, and wherein the annotated portion of the diagnostic image is inserted into the medical report in response to receipt of the natural language input.

14. A system, comprising:
an input device;
one or more processors;
one or more non-transitory computer-readable media having stored thereon instructions that, upon execution by one or more processors, cause the one or more processors to:
receive medical image data for a diagnostic image of a patient;
identify, using a computer vision algorithm, a computer-selected anatomical feature of the patient and an image of the computer-selected anatomical feature within the diagnostic image of the patient;

store an output of the computer vision algorithm that identifies the image of the computer-selected anatomical feature;

receive natural language input from the input device, the natural language input comprising report information and report generation instructions, wherein the report information identifies a physician selected anatomical feature of the patient;

identify, using a natural language processing algorithm, the report information and the report generation instructions in the natural language input;

determine whether the physician selected anatomical feature matches the computer-selected anatomical feature; and in response to the physician selected anatomical feature matching the computer-selected anatomical feature, generate a medical report for the patient that includes the image of the computer-selected anatomical feature and is based at least in part on the report generation instructions.

15. The system of claim 14, wherein:
the input device comprises a microphone of a mobile device,
the natural language input comprises dictated information detected by the microphone; and
the mobile device in communication with a computing device that comprises the one or more processors and that is separate from the mobile device.

16. The system of claim 15, wherein the mobile device comprises an interface for interacting with and controlling at least one operation of the computing device from the mobile device.

17. The system of claim 14, wherein identifying the image of the computer-selected anatomical feature comprises determining a cropping window that does not cross a gradient within the diagnostic image and the diagnostic image is cropped to identify the image of the computer-selected anatomical feature.

18. The system of claim 14, wherein:
the computer-selected anatomical feature is identified based on an association with an annotation; and
identifying the image of the computer-selected anatomical feature comprises determining a cropping window surrounding the computer-selected anatomical feature in the diagnostic image, wherein the cropping window is shaped and positioned such that a perimeter of the cropping window does not cross a gradient within the diagnostic image.

19. The system of claim 14, wherein the medical report is stored as a JavaScript Object Notation (JSON) file.

* * * * *